Dec. 10, 1935. J. H. NICOLAS Plant Pat. 160
ROSE
Filed Aug. 22, 1935
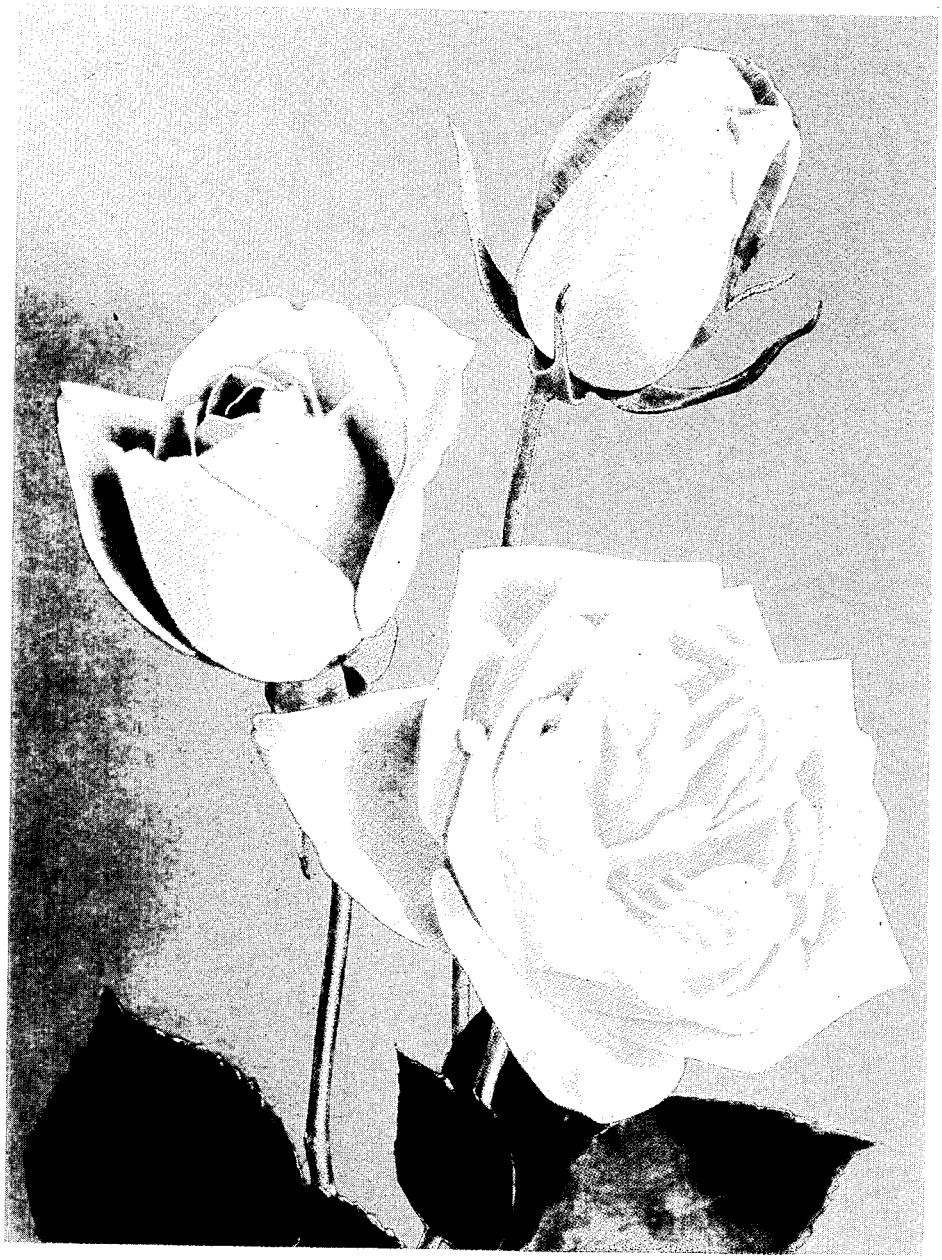
Inventor
J. H. Nicolas
By Robb & Robb
attorneys Patented Dec. 10, 1935 Plant Pat. 160

UNITED STATES PATENT OFFICE

160

ROSE

Jean H. Nicolas, Newark, N. Y., assignor to
Dixie Rose Nursery, Tyler, Tex.

Application August 22, 1935, Serial No. 37,385

1 Claim. (Cl. 47—61)

The present invention relates to a new and distinct variety of rose plant, the result of a definite breeding in an effort to unit the two famous perfumes of the well known varieties "La France" and "Marechal Niel."

This objective naturally involved the problem of overcoming the difficulties arising from the facts that the rose "La France" is notoriously a sterile seed bearer and the rose "Marechal Niel" is practically so, at least in the north, and its rare seeds are poor in germination. To this end, I selected a prolific seed bearing variety, namely, the "Emile Charles" rose, the color combination of which stands the nearest to the probable one resulting from a mixture of "La France" and "Marechal Niel", and pollenized it with "La France."

From this cross, I then selected the most La France-like seedling and pollenized it with "Marechal Niel."

Among the seedlings of this last cross I found one of a different plant character than the usual hybrid tea, and it is this one which constitutes the new variety of the present invention. Its distinctions reside in the facts that it is a vigorous bush of the shrub type, eventually reaching in mild wintered sections the height of six or seven feet branching into proportionate width and blooming continuously; the bloom is semi-large, opening flat and somewhat quartered similar to the old well known variety Souvenir de la Malmaison; and in color it is a luminous pink with an abundant suffusion of salmon overcast with amber.

So far as the perfume of this new variety is concerned, the object in view was attained as the odor thereof is unique in the sense that it is a blend of both those of La France and Marechal Niel.

Considering all of the foregoing factors, the present invention represents a new type of ever-blooming rose shrub of great value as specimen or for landscape work, as well as mass or hedge planting while also being amenable to pruning for bedding purposes. As the blooms come singly on long stems, it also has considerable value for cut flowers.

This new variety is particularly valuable for growing in the south, but it is found to stand northern winters also when given adequate protection.

A sexual reproduction of the new plant show it to reproduce true to form.

The above mentioned and other important characteristics are here listed for detail information, all color designations being in accord with the Gravereaux system:—

Parentage:
*Seedling.*
*Seed parent*—Emile Charles X La France.
*Pollen parent*—Marechal Niel.

Classification:
*Botanic and commercial*—Hybrid Tea.

*Flower*

Blooming habit:
Continuous.

Bud:
*Size.*—Large.
*Form.*—Long, ovoid; unaffected by wet or hot weather.
*Color.*—When sepals first divide—pink with orange overcasting. When petals begin to unfurl—pink with orange at base. When half blown: Inside of petals—salmon pink; reverse side of petals—a shade darker.
*Sepals.*—Smooth edge; curl back when bud half open.
*Calyx.*—Shape—apple. Size—broad. Aspect—smooth. Odor when rubbed—none.
*Peduncle.*—Length—long. Aspect—smooth. Color—green. Strength—erect, slender.
*Opening.*—Opens well and is unaffected by adverse conditions.

Bloom:
*Size.*—Medium; average size when fully expanded 3½ inches.
*Borne.*—Singly.
*Stems.*—Long, normal strength.
*Form.*—When first open, flat, somewhat quartered.
*Permanence.*—Retains form to the end.
*Petalage.*—Very double (many petals and stamens hidden).
*Color.*—Center of flower—luminous pink with heavy suffusion of amber. Outer petals—pink with overcast of orange. Base of petals (aiglets)—yellow. Outside of petals—salmon pink with suffusion of amber. Reverse of petals—deeper pink. General tonality at a distance—salmon pink.
*Variegations.*—None.
*Discoloration.*—General tonality first, second and third days—salmon pink.

Petals:

*Texture.*—Thick; unaffected by wet or hot weather.

*Appearance.*—Inside satiny; outside shiny.

*Form.*—Round; center ones are pointed with crease in middle.

*Arrangement.*—Quartered—petaloids in center many, small.

*Persistence.*—Hang on and dry.

*Fragrance.*—Strong. Nature—a blend of old rose and tea.

*Lasting quality.*—On the plant and as cut flowers very long.

Genital organs:

*Stamens, anthers.*—Few. Color—yellow. Arrangement—mixed with petaloids.

*Stamens, filaments (threads).*—Short. Color—yellow.

*Pollen.*—Gold yellow.

*Styles.*—Loosely separated, short, thin.

*Stigmas.*—Color—white.

*Ovaries.*—Some protruding from calyx.

Fruit:

Variety is generally sterile with its own pollen; more fertile with foreign pollen.

*Form.*—Round.

*Aspect.*—Smooth.

*Color at maturity.*—Russet brown.

*Sepals.*—Caducous (soon falling).

*Plant*

Form:

Bush or shrub.

Growth:

Very vigorous, branching.

Foliage:

Five or seven leaflets.

*Size.*—Large.

*Quantity.*—Abundant.

*Color.*—New foliage—upper side—light green; under side—green. Old foliage—upper side—normal green; under side—lighter green.

*Shape.*—Oval pointed or lanceolate.

*Texture.*—Upper side leathery. Under side smooth. Ribs and veins—prominent.

*Edge.*—Serrated (saw toothed).

*Serrations.*—Single, large.

*Rachis.*—Color green, under side smooth.

*Stipules.*—Long, smooth.

*Disease resistance.*—Resistant.

Wood:

*New wood.*—Color—light green. Bark—smooth.

*Old wood.*—Color—green. Bark—smooth.

Thorns: (Divided into thorns, prickles, and short needles).

*Thorns.*—Quantity—on main stalks from base, few; on laterals from stalks, few. Form—broad base, medium length, hooked downward. Color when young—green. Position—irregular.

*Prickles.*—Quantity—on main stalks, none; on laterals, none.

*Short needles.*—Quantity—on main stalks, none; on laterals, none.

I claim:—

A new and distinct type and variety of rose plant, as shown and described, characterized by its adaptability for everblooming specimen, landscape work and mass or hedge planting, while also being amenable to pruning for bedding purposes, the distinctiveness of the fragrance and color of its blossom and the growth of blooms on single long stems.

JEAN H. NICOLAS.